United States Patent [19]

Boinot et al.

[11] Patent Number: 4,725,231
[45] Date of Patent: Feb. 16, 1988

[54] DENTAL-SURGEON HANDPIECE WITH BATTERY LIGHTING

[75] Inventors: Jean-Claude Boinot, Roulans; Jean-Paul Jacoulet, Besancon, both of France

[73] Assignee: Micro-Mega S.A., Besancon, France

[21] Appl. No.: 844,358

[22] Filed: Mar. 26, 1986

[30] Foreign Application Priority Data

Mar. 27, 1985 [FR] France ............... 85 05017

[51] Int. Cl.$^4$ .............................................. A61C 1/00
[52] U.S. Cl. ...................................................... 433/29
[58] Field of Search ................................. 433/29, 126

[56] References Cited

U.S. PATENT DOCUMENTS

| | | | |
|---|---|---|---|
| 3,109,238 | 11/1963 | Marks | 433/29 |
| 3,509,629 | 5/1970 | Kidokoro et al. | 433/116 |
| 4,561,845 | 12/1985 | Meller | 453/29 |
| 4,600,384 | 7/1986 | Olsen | 433/29 |

FOREIGN PATENT DOCUMENTS 1068425 10/1955 Fed. Rep. of Germany ........ 433/29

Primary Examiner—Robert Peshock
Attorney, Agent, or Firm—Robert E. Burns; Emmanuel J. Lobato

[57] ABSTRACT

This equipment for dental surgeons comprises a handpiece incorporating at least one bulb for illuminating the treatment area and an endpiece housing a battery. This endpiece comprises on its front end a pair of spring-loaded contact studs adapted to engage with corresponding concentric tracks formed on the rear face of the handpiece for energizing the bulb. The battery is rechargeable by means of a device comprising two concentric tracks of same diameter as the handpiece tracks and connected to a circuit adapted to switch automatically between a quick-charging condition and a slow-charging condition according to the voltage developed across the battery terminals.

31 Claims, 8 Drawing Figures

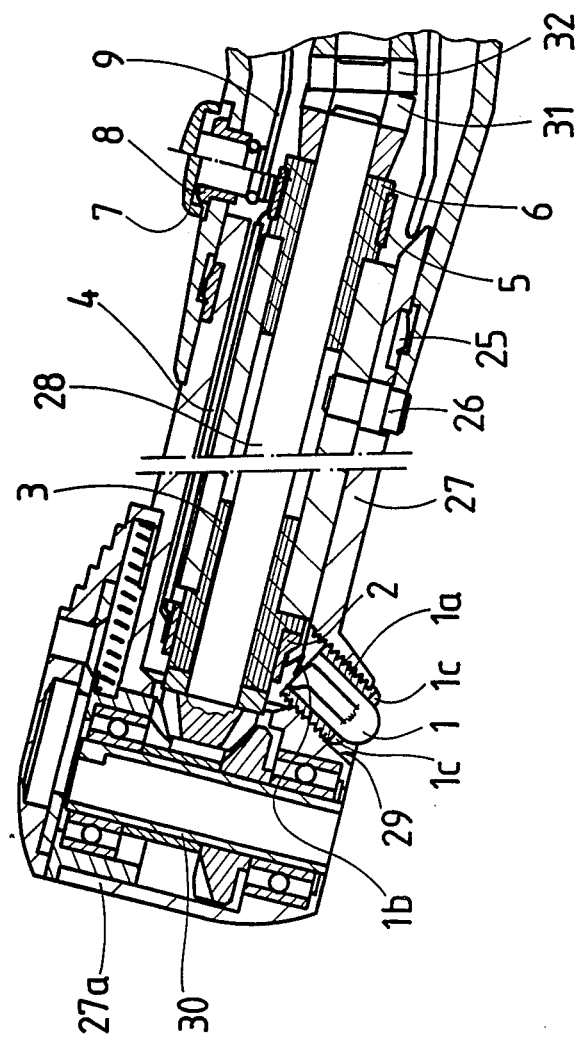

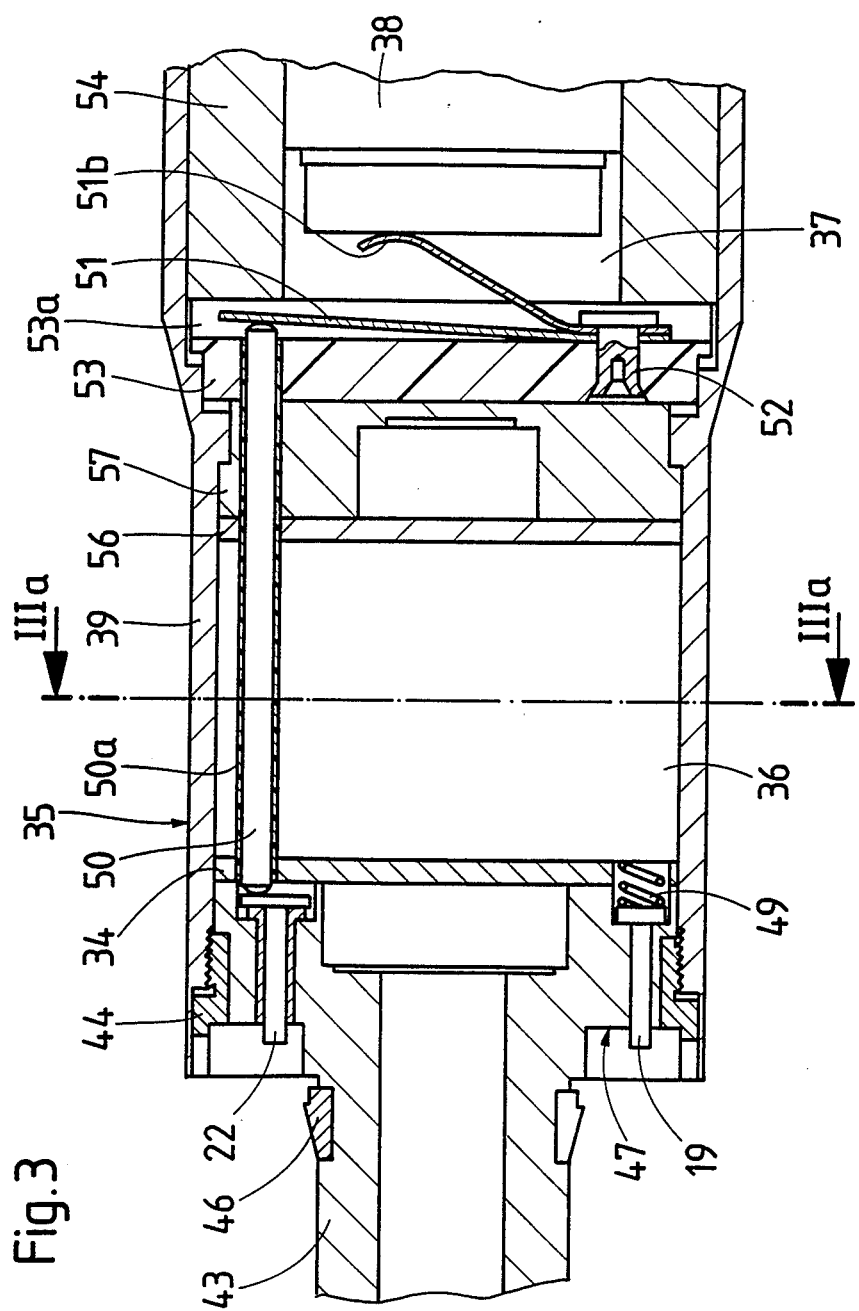

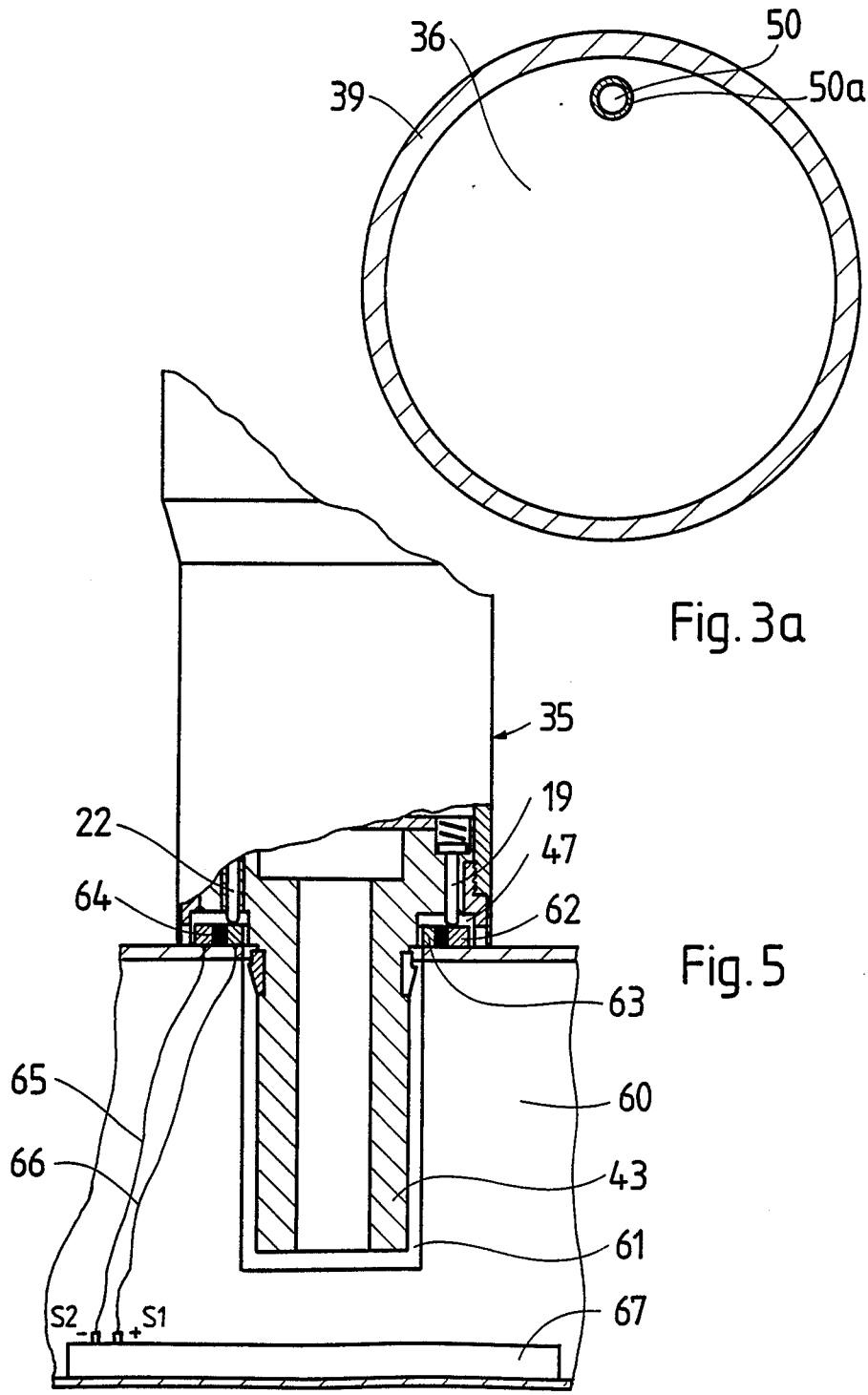

DENTAL-SURGEON HANDPIECE WITH BATTERY LIGHTING

FIELD OF INVENTION

The present invention relates in general to dentists' equipment and specifically relates to an improved handpiece comprising at least one bulb for illuminating the treatment area and an endpiece containing a battery and adapted to be connected to the rear end of the handpiece, this endpiece being provided at its front end with a projection adapted to fit into the handpiece.

THE PRIOR ART

A known proposition aiming to facilitate the dental-surgeon's task consisted in incorporating lighting means in the handpiece for illuminating the treatment area in the patient's mouth. In the case of a contra-angle handpiece, the shaft for driving the tool or instrument clamped in the head of the contra-angle is driven by a pneumatic or electric micromotor housed in an endpiece adapted to be connected to the rear end or handle of the handpiece. The micromotor shaft extends forwardly from the endpiece so as to be drivingly coupled to the rear end of the handpiece driving shaft. The bulb housed in the contra-angle head is energized by means of a battery housed in the micromotor containing endpiece, this battery delivering for example a 6-Volt D.C. This arrangement is disclosed in a co-pending patent application filed on May 20, 1985 by the same applicants. However, this battery has a relatively short effective life and provides a sufficiently bright lighting during only about two hours. Now this can be regarded as constituting a serious inconvenience for the dental surgeon confronted with frequent replacements of discharged batteries.

SUMMARY OF THE INVENTION

It is the primary object of the present invention to avoid the above-described inconvenience by providing a handpiece for dental-surgeons which comprises a rechargeable battery and assembly means that are simple and easily handled by the dentist, so that detrimental losses of time are safely avoided.

For this purpose, the dentist's equipment according to the present invention is characterized by the fact that the endpiece associated with the front hand-piece is provided at its front end with spring-loaded contact studs connected to the two poles or terminals of the battery, the contact means at the rear end of the front handpiece consisting of concentric annular tracks resiliently engaged by the spring-loaded contact studs when the two members are assembled or coupled with each other, that said battery is of the rechargeable type and that a battery charger is also provided, this battery charger comprising in its upper portion a cavity adapted to be engaged with the projection and surrounded by a pair of concentric annular tracks constituting the output contacts of same diameter as the annular tracks formed on the rear face of the front handpiece, said last-mentioning pair of concentric annular tracks being engaged with the spring-loaded contact studs when the endpiece is fitted to the front handpiece with its projection engaged in the cavity.

Thus, the practiner has at his disposal an apparatus of relatively simple construction which can be used very easily. Since, as a rule, burring operations require relatively little time, the contra-angle is provided preferably with a switch, as described in the above-mentioned co-pending patent application, so that the dentist can switch on the light only when necessary. Since the actual working time in a half-day is usually less than two hours, the dental surgeon, at the end of each working period, for example at noon or in the evening, can load the endpiece on the charger for recharging the battery. This rechargeable battery, consisting of five cells, has a diameter of about 16 mm and a length of about 32 mm, and can be housed in a cavity provided for this purpose in the endpiece, preferably behind the micromotor. In the case of a turbine-type handpiece, without micromotor, the endpiece encloses only the battery and the compressed-air supply, the compressed air being fed directly to the handpiece head. In the case of an old-type handpiece driven in the conventional manner by means of an external electric motor via a pulley and belt transmission, the endpiece contains means for converting the motion and also the battery.

The charger supplyied with electric current from the main source may be either disposed near the dental unit, or incorporated in support means provided for supporting the handpiece on the dental unit.

According to a preferred form of embodiment of the present invention, the battery is housed in a cavity located behind the motor unit, the ground contact being obtained via a battery supporting socket through conducting elements of the motor unit. The other contact is obtained via a pair of resilient blades bearing the one against the positive terminal of the battery and the other against an insulated conducting rod slidably mounted in a recess extending along the motor unit, the opposite end of the rod urging the spring-loaded contact stud forwards.

The battery charger comprises preferably circuit means for switching automatically from a quick-charge operation to a slow-charge position, according to the voltage existing across the battery terminals, the circuit comprising an operational amplifier adapted to compare the battery voltage with an adjustable threshold voltage, the amplifier having two operating conditions according to the battery voltage. In a first condition, a high-current charging circuit is formed, and in the other condition, a low-current charging circuit is obtained.

The invention will now be described with reference to the accompanying drawings illustrating a typical form of embodiment thereof which comprises a contra-angle handpiece, an endpiece and the charging device.

BRIEF DESCRIPTION OF THE DRAWINGS

FIG. 1a is a fragmentary longitudinal section showing the front portion of the handpiece with the contra-angle head fitted thereto;

FIG. 3 is a longitudinal section showing the front portion of the endpiece;

FIG. 3a is a sectional view showing the endpiece, the section being taken along the line III—III of FIG. 3;

FIG. 5 is a fragmentary diagrammatic and sectional view of the endpiece supported by the battery charger.

DESCRIPTION OF THE PREFERRED EMBODIMENTS

Figure 1B:
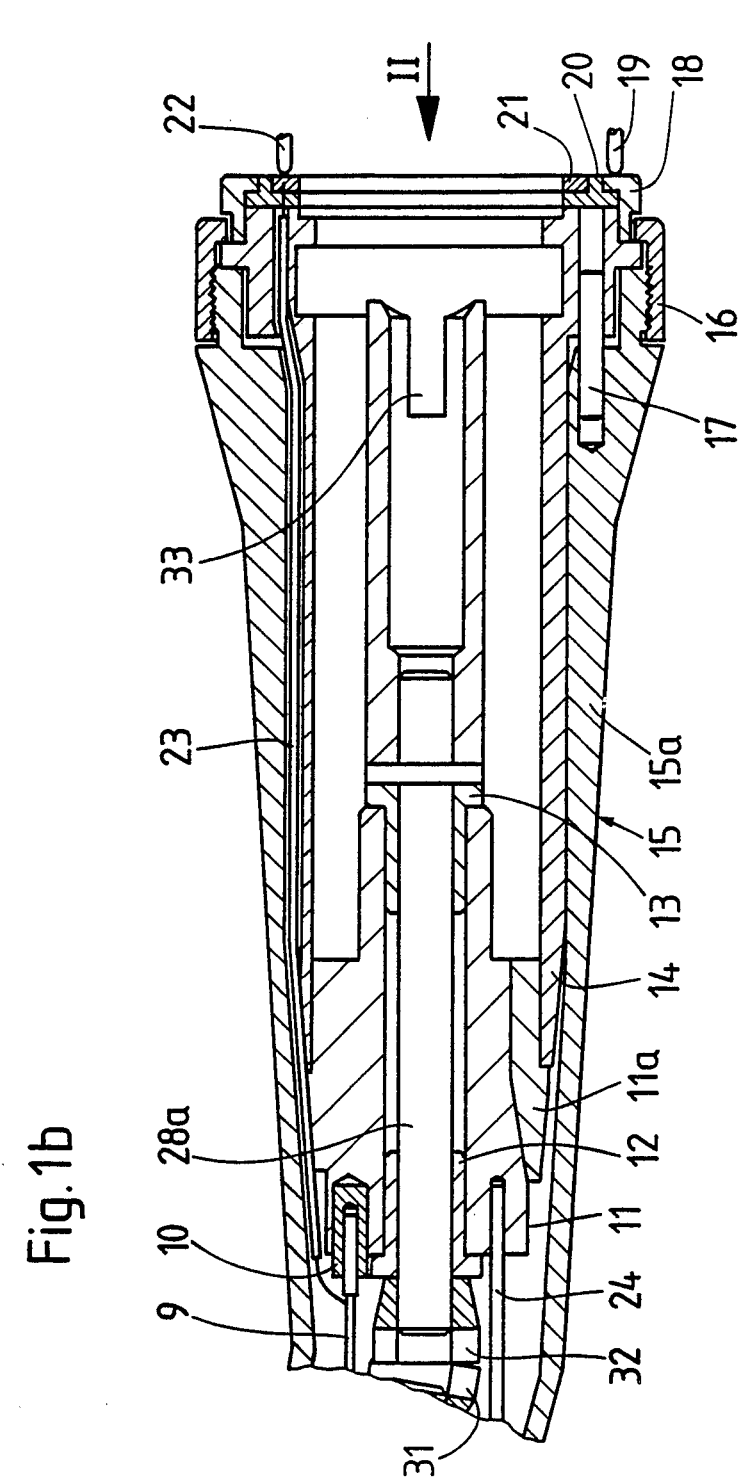
FIG. 1b is a view similar to FIG. 1a but showing the rear portion of the handpiece.

The contra-angle dental handpiece illustrated in the drawings comprises separate front and rear pieces. The front piece consists in the known fashion of a handle or rear section 15 and a front section 27 incorporating the head 27a in which a tool (not shown) is adapted to be fitted in a tool holder 30. This tool holder 30 is driven as conventional by a rotary shaft 28 housed in the front section 27 and provided at its rear end with a pinion 31 adapted to mesh with a corresponding pinion 32 fixed to the front end of another shaft 28a rotatably mounted in the handle 15. This shaft 28a, in the example illustrated, is adapted to be driven by a micromotor (not shown) secured to the rear end of handle 15. In this case, the nose of the micromotor protrudes into the handle and its output shaft is in driving engagement with the fork 33 formed at the rear end of shaft 28a. The front section 27 is forcibly fitted in the outer cover 15a of handle or rear section 15 and rigidly connected thereto by means of a circlip 25 and positioned circonferentially by a radial pin 26 secured to the head 27a.

A cavity 29 formed in the head 27a is adapted to receive an electrical midget bulb 1 cemented or crimped in a conducting holder 1a screwed in the head 27a. This holder 1a has two diametral slots 1c formed therein so that it can be screwed in or out by means of a suitable screwdriver. The angle of inclination of the recess 29 relative to the tool axis is such that the light rays emitted by the bulb 1 are directed towards the treatment area at the tool end. The ground terminal of bulb 1, that is, the outer socket of the bulb base, is held in close contact, for example by welding, with the bulb holder 1a which engages in turn the shank of the ground-forming front section 27 also made from a suitable conducting metal. The other terminal 1b of bulb 1, which is the central contact of the bulb base, engages with a metal ring 2 crimped on a support 3 of insulating material acting as a front bearing or support for a bearing in which the shaft 28 is rotatably mounted. This ring 2 is supplied with electric current through an insulated wire 4 having one end welded to the ring 2 and the other end welded to another metal ring 5 crimped in turn to another insulating support 6 acting as a rear bearing or support for another bearing for the shaft 28.

Since the front section 27 must be separated from the handle or rear section 15, the current is fed to this second ring 5 via a resilient contact 9 consisting of a spring blade having one end embedded in an inner conducting socket 11 forming an integral part of the handle 15. This resilient contact 9 extends axially and can be caused to engage with the ring 5 of front section 27 at will through a switch 7 of the push-knob type which is slidably fitted in a ring 8 embedded in turn in the outer cover 15a of handle 15. The push-knob head is mushroom-shaped to prevent the ingress of dust and foreign substances from entering into the contra-angle. When the push-knob 7 is depressed by one of the fingers of the user's hand holding the handpiece, the spring blade 9 is deflected and moved towards the ring 5, thereby closing the contact. Therefore, the dental surgeon can turn the light on only when necessary, without necessarily actuating the tool at the same time. The circuit is opened automatically when the contra-angle is released, because the push-knob 7 returns automatically to its inoperative position by the spring blade 9 acting as a return spring. Thus, the operator has the certainty that when the contra-angle is not in use the bulb will remain deenergized.

The spring blade 9 is supplied with current by means of an insulated conducting wire 23 housed in a groove formed in an inner sleeve 14 of conducting metal. The front end of wire 23 is welded to the spring blade 9 and its rear end is in electrical contact with an annular conducting track 21 surrounding concentrically the shaft 28a and constituting the rear end of the handle.

Figure 2:
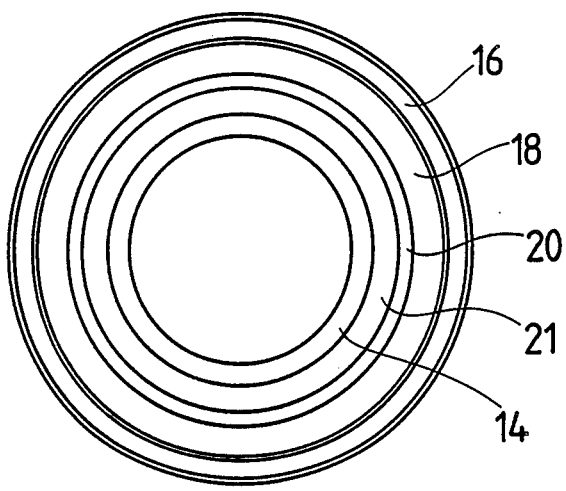
FIG. 2 is an end view taken in the direction of the arrow II of FIG. 1b.

The other electric line constituting the ground consists of an inner socket 11 and the inner sleeve 14 of conducting metal which are fitted in the handle 15. The socket 11 is embedded in the inner sleeve 14 so as to be in sliding contact engagement therewith, and these component elements 11 and 14 are assembled by means of a ring nut 16 locked against rotation or release by a pin 17. On the rear surface of handle 15, of the front piece the ground line terminates with an annular track 18 consisting of a metal ring surrounding concentrically the other annular track 21 and secured to the inner sleeve 14 so as to hold in position an insulating ring 20 separating the ring track 18 from the track 21 (FIGS. 1b and 2).

Mounted in the socket 11 are two bearings 12,13 in which the shaft 28a is rotatably mounted. In addition, an orifice is formed in socket 11 in case the circulation of a cooling fluide were contemplated. In the example illustrated, this orifice is closed by a metal plug 11a. Preferably, the outer cover 15a is made of light alloy. To ensure an efficient contact between the conducting body of the front section 27 and the socket 11 of handle 15, a resilient contact 24 is provided, for example, in the form of a rod embedded at its rear end in socket 11 and curved at the front end so as to constantly engage with a bevelled portion of the body of front section by deflecting the rod 24 to thereby provide a good electrical contact. Thus, a simpe yet efficient and reliable electrical connection is obtained between the two sections of the contra-angle while permitting the easy and quick assembly and disassembly thereof by firstly pulling the front section 27 out of the handle 15, this movement causing the circlip 25 to yield inwards, and by subsequently extracting from the handle 15 the complete assembly enclosed in socket 14 by releasing the nut 16. Moreover, the same handle 15 can be used with different heads.

The handpiece is driven by means of a suitable pneumatic or electric mircomotor housed in an endpiece or rear piece 35 (FIGS. 3 and 4) adapted to be connected to the rear end of handle 15 of the front piece during use of the dental handpiece and comprising two contactcs 19 and 22, respectively, consisting of spring-loaded pistons and adapted to engage with the separate annular tracks 18 and 21, respectively, formed in the rear end of handle 15. The electric current for energizing the bulb 1 is supplied by a rechargeable battery 38 housed in the endpiece 35.

Figure 4:
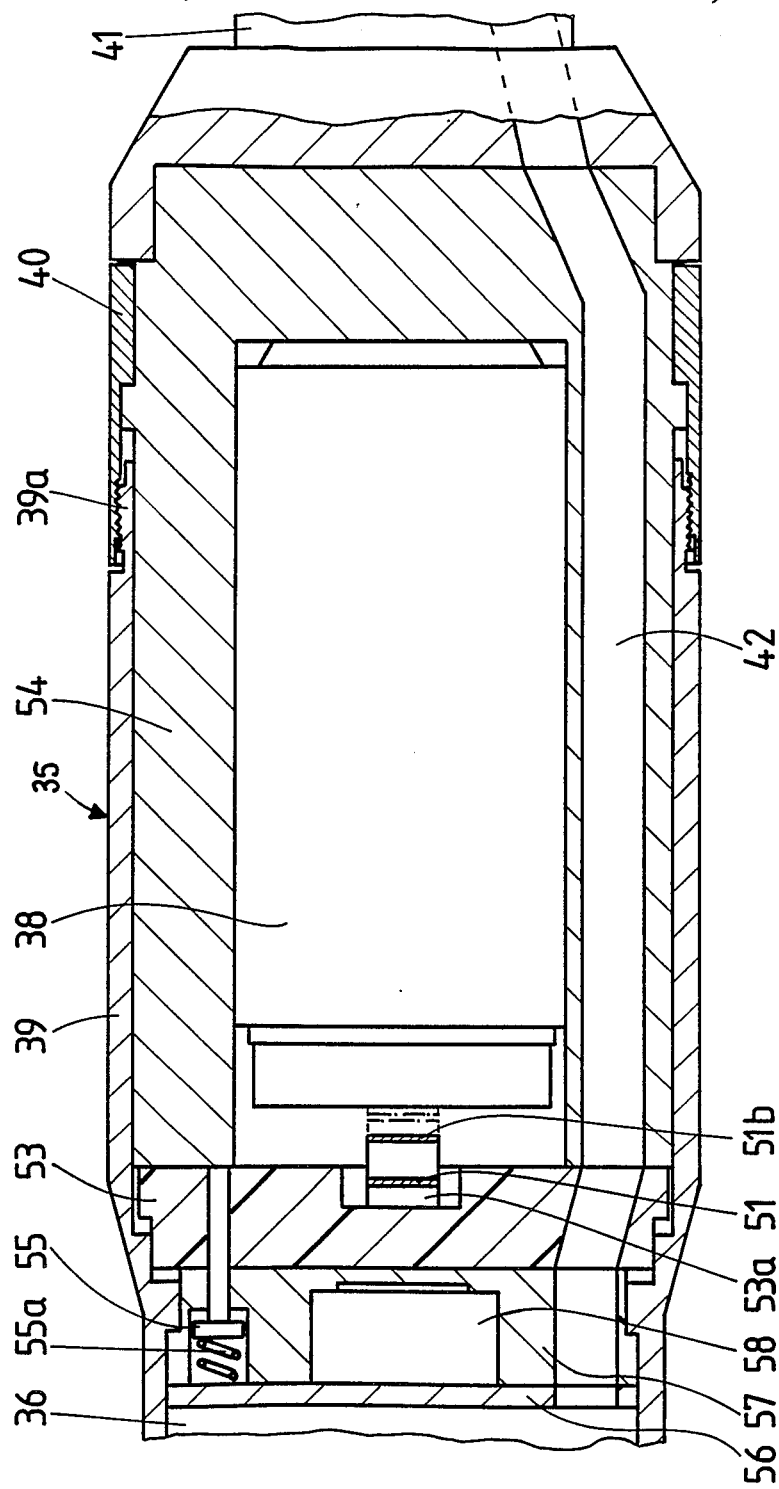
FIG. 4 is a longitudinal section, taken along a different plane of the rear portion of the endpiece.

FIGS. 3 and 4 of the drawings illustrate a typical form of an embodiment of the endpiece or rear piece 35 housing the motor unit 36 disposed between lateral plates 34 and 56, and rearwardly from this motor unit, a cavity 37 is provided to receive the battery 38. In this example, the battery 38 housed in cavity 37 has a diameter of about 16 mm and a length of about 32 mm. This 6-Volt battery is capable of supplying a sufficiently bright lighting during ca. 2 hours.

The endpiece 35 consists of a front socket 39 having a screw-threaded rear end 39a adapted to be engaged by an internally-threaded rear socket 40 provided with a ring 41 for coupling this rear socket 40 to a current supply pipe. In the embodiment illustrated, the motor 36 is a pneumatic motor of known type having its blades driven by compressed air supplied from an external compressor via the coupling device 41 and two-way pipes 42 (FIG.4).

The endpiece 35 is provided at its front end with a hollow projection 43 secured by means of a nut 44. The output shaft (not shown) of the micromotor extends through this projection 43 constituting the nose of the micromotor. The projection 43 is adapted to be inserted into the rear end of the handle 15 and fastened thereto by means of a spring-ring 46 of the known type. The front face of endpiece 35 has an annular groove 47 formed therein, and the annular tracks 18,21 of handle 15 are adapted to fit in the groove 47. The piston-like spring-loaded contact studs or pins 19,22 project at a certain distance from the bottom of the annular groove 47.

The ground contact pin 19 urged by a spring 49 projects from the radially outer side of annular groove 47 and engages with the annular track 18, and the other contact pin 22 projects from the radially inner side of annular groove 47 and engages with the other annular track 21 of handle 15 of the front piece when the front and rear pieces are coupled with each other such that the pair of pins 19, 22 electrically and physically contact with the pair of annular tracks 18, 21 with a positional allowance for relative circumferential displacement therebetween.

The rear portion of contact 22 bears against a conducting rod 50 insulated by a sheath 50a. This rod 50 is slidably mounted in a passage formed through the lateral plate 34, the motor unit 36, the lateral plate 56, an insulating ring 53 and a rear bearing carrier 57 (shown only diagrammaticaly) supporting the rear bearing 58 of motor 36. The rear end of rod 50 bears against a resilient blade 51 of conducting metal housed in an annular groove 53a formed in the insulating ring 53. This resilient blade 51 is connected by a rivet 52 to another resilient blade 51b bearing resiliently against the positive terminal of battery 38, the rivet 52 being clinched in the insulating ring 53. The resilient blade 51 exerts an axial resilient pressure against the sliding rod 50 pressed in turn against the contact 22, so that this contact 22 is constantly urged resiliently axially outwards.

The other spring-loaded contact 19 constituting the ground or negative contact is fed with energizing current via the battery supporting socket 54 which, when the sockets 39 and 40 are assembled with each other by means of their screw-threaded portions, engages with a contact 55 urged by another spring 55a. This contact 55 bears against the metal lateral plate 56 engaging with in turn one conducting metal portion of motor 36 in order to establish an electric connection with the spring-loaded contact 19 (FIG. 3).

Figure 6:
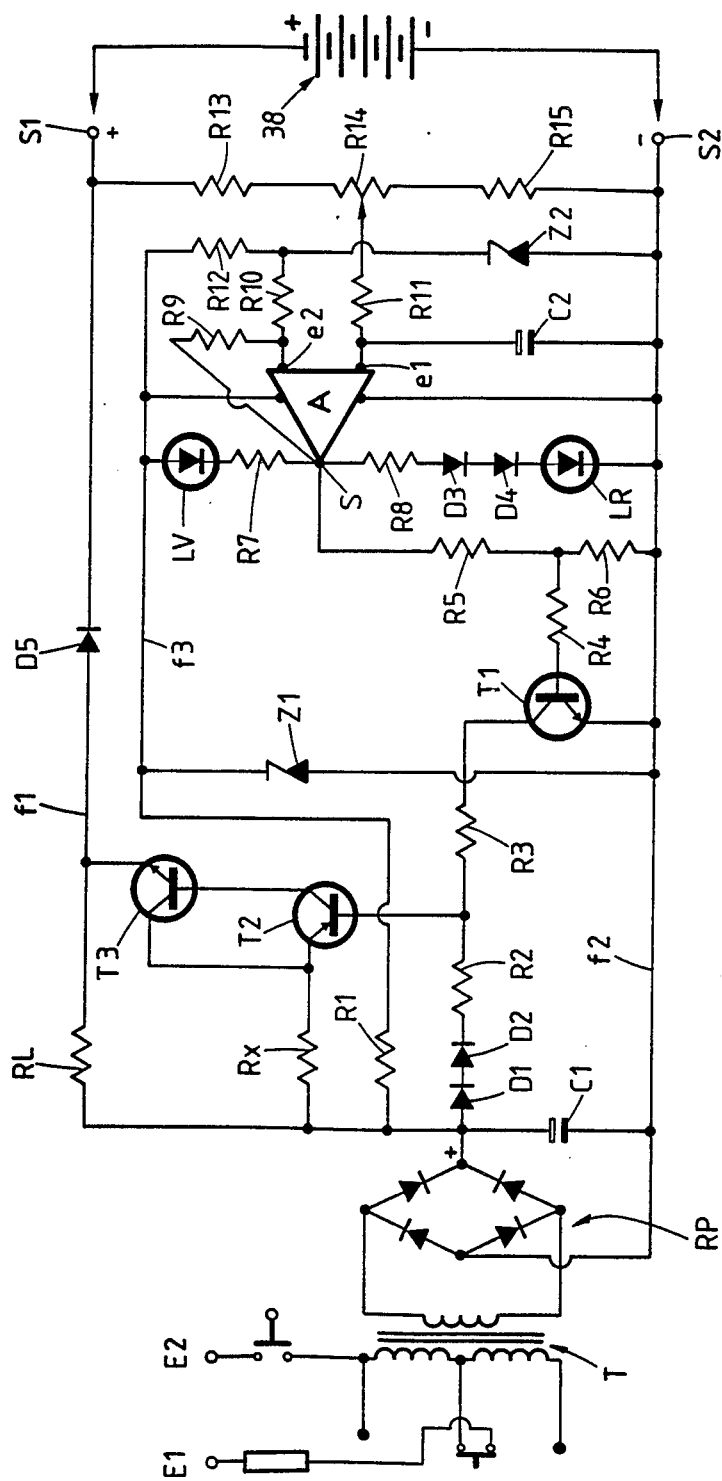
FIG. 6 is a wiring diagram showing the electric circuit of the battery charger.

When the handpiece is not used, or when the battery 38 is discharged, the practitioner loads the endpiece 35 upon a battery charger shown diagrammatically in FIG. 5. This battery charging device comprises a base plate 60 having a cavity 61 opening at its top surfac. The depth of this cavity 61 conforms to the length of the above-mentioned projection 43 of endpiece 35, that is, in the example illustrated, to the length of the micromotor nose. Two conducting concentric annular tracks or rings 62,63 separated by an insulating ring 64 surround the cavity 61. These tracks or rings have exactly the same dimensions as the conducting tracks 18,21 provided at the rear end of the handle 15 so as to penetrate into the annular groove 47 of endpiece 35 and thus engage with the corresponding springloaded contact studs 19,22 irrespective of the angular position of the endpiece about its longitudinal axis. Under these conditions, the dental surgeon is not required to pay any particular attention to the way in which he puts the instrument on the battery charging device. The aforesaid concentric tracks 62,63 are connected via conductors 65,66 to the output terminals S2,S1, respectively, of an electronic circuit 67 shown diagrammatically in FIG. 6 to which reference will now be made for a detailed description hereinafter.

This electronic circuit 67 operates to switch automatically from quick charging operation to slow charging operation, and vice versa, according to the voltage across the terminals of battery 38. The circuit comprises two input terminals E1, E2 connected to a transformer T adapted to be supplied with 110-V or 220-V main power. The output current of this transformer T is fed to a bridge rectifier RP connected in turn to an integrated circuit having constant-current characteristics for two current values, this circuit comprising an operational amplifier A operating as a voltage comparator. This circuit comprises output terminals S1,S2 connected to the concentric tracks 63,62 formed on the top surface of the base plate 60 of charging device adapted to receive the endpiece 35 of which the battery needs a new charge.

A capacitor C1 is connected across the negative and positive terminals of bridge rectifier RP, the negative terminal being connected via a line f2 to the negative output terminal S2 of the electronic circuit.

The positive terminal of bridge rectifier RP is followed by a pnp-type transistor T2 having a resistor Rx inserted in its emitter circuit, this transistor T2 being cascade-connected to another transistor T3 of the npn type; the emitter of transistor T2 is connected via a conductor f1 comprising a diode D5 to the positive output terminal S1. This diode D5 protects the circuit against any undesired inversion of the battery polarity. A resistor RL is connected in parallel with resistor Rx and transistor T2. The base circuit of transistor T2 comprises two series-connected diodes D1,D2 and a resistor R2 for biasing said transistor T2, followed by another resistor R3 connected to the collector circuit of an npn transistor T1. The base of this transistor T1 is connected via a resistor R4 to a voltage divider consisting of resistors R5 and R6 connected in turn to the output S of the amplifier A.

The operating voltage of amplifier A is obtained by means of a resistor R1 connected to the positive terminal of bridge rectifier RP and to a conductor f3; a Zener diode Z1 is connected between conductor f3 and line f2 giving a constant operating voltage.

The supply terminals of amplifier A are connected to conductors f3 and f2. The amplifier output S is connected to a voltage divider consisting of the series-connected circuit comprising, between conductors f3 and f2, a first electroluminescent diode (LED) LV acting as a pilot light, a resistor R7, another resistor R8, a pair of diodes D3 and D4 providing a constant voltage drop, and a second electroluminescent diode (LED) LR, acting as a pilot light, the output S being connected to the common terminal of resistors R7 and R8.

The operational amplifier A has two inputs e1 and e2, that is:

input e1 is connected via a resistor R11 to a voltage divider across the output terminals S1 and S2, the voltage divider comprising a resistor R13, a potentiometer R14 having its sliding contact connected via resistor R11 to input e1, and another resistor R15.

A capacitor C2 is mounted between input e1 and conductor f2:

input e2 is connected via a resistor R10 to a voltage divider disposed between conductors f3 and f2, this voltage divider consisting of a resistor R12 and a Zener diode Z2 providing a constant voltage drop and consequently a fixed voltage at input e2.

The operational amplifier A operates to compare the voltage value of the battery 38 connected across terminals S1 and S2 with a threshold value defined by the voltage divider and adjustable by means of the potentiometer R14.

The above-described device operates as follows:

When the battery voltage is low, therefore when the current flowing across outputs S1 and S2 through resistors R13 and R15 and potentiometer R14 is low, the voltage measured at potentiometer R14 and delivered to the input e1 of amplifier A is more negative than the reference potential at the other input e2. The output S of amplifier A is positive and the current flows through diode LR, producing, for example, a red light for indicating that the charge current is relatively high, the other diode L, giving, for example, a green light, remaining deenergized. The current flows through resistors R5 and R6, thereby biasing transistor T1 to its conductive state, and the other transistors T2 and T3 are acocrdingly switched to their conductive state; under these conditions, the charging current flows through resistor Rx, thus defining a relatively high charging current, for example, of the order of 12 mA, passing through transistor T3 and causing the battery 38 to be rapidly charged through its terminals S1,S2.

If, on the contrary, the battery voltage is high, the voltage at R14 and at input e1 is more positive than the voltage at input e2, the output S of amplifier A is negative and a current is generated via the other circuit section through the now energized diode LV and resistor R7. The bias voltage at the base of transistor T1 is zero, this transistor being thus locked together with transistors T2 and T3. A relatively low charging current, for example, of the order of 6 mA, flows through the resistor RL and diode D5 to output S1, thus charging the battery 38 at a slow rate. This condition is indicated by the green light of diode LV.

Of course, the present invention should not be construed as being a strictly limited by the specific form of embodiment shown and described herein, from the dual point of view of the endpiece and circuit structures, as well as of the type of handpiece. If the handpiece is designed for being driven in a conventional manner not by a micromotor but by an external motor via a pulley and belt transmission, in this case the element carrying the electric contact means is a coupling endpiece incorporating the movement converter and the battery. In the case of a turbine handpiece, the endpiece comprises conduit means for supplying compressed air and the battery.

What is claimed is:

1. In combination: a dental handpiece comprising a front piece at the front end portion thereof a tool holder for rotatably driveably supporting a tool and a bulb for illuminating an operating range of the tool during use of the dental handpiece, a rear piece separably engageable with the rear end of the front piece at the front end of the rear piece during use of the dental handpiece, the rear piece having therein a rechargeable battery for supplying electric power to the bulb, and a projection extending longitudinally forwardly from the front end of the rear piece and being insertable into the front piece when the front and rear pieces are coupled with each other, and connecting means for electrically connecting the front and rear pieces with each other when the front and rear pieces are coupled with each other, the connecting means having a pair of spring-loaded contact studs electrically connected to the terminals of the battery and extending longitudinally forwardly from the front end of the rear piece, and a pair of concentric annular tracks electrically connected to the terminals of the bulb and disposed at the rear end of the front piece such that the annular tracks make electrical contact with respective ones of the contact studs with a circumferential allowance therebetween when the front and rear pieces are coupled with each other; and a battery-charging device for removably receiving therein the rear piece to charge the battery during other than use of the dental handpiece, the battery-charging device having means defining a cavity therein configured to conform to the projection which extends from the front end of the rear piece, and a pair of concentric annular terminals disposed around the opening of the cavity and configured to correspond to the concentric annular tracks such that the concentric annular terminals make electrical contact with respective ones of the contact studs with circumferential allowance therebetween when the projection of the rear piece is inserted into the cavity of the battery-charging device during charging of the battery.

2. The combination according to claim 1 wherein the rear piece includes a micromotor disposed therein and connectable to the tool holder of the front piece when the front and rear pieces are coupled with each other for driving the tool holder, a recess provided in the rear piece rearwardly from the micromotor for receiving therein the battery, first means for electrically connecting one of the contact studs to a ground terminal of the battery, the first means including an electrically conductive battery-supporting socket disposed in the cavity for supporting therein the battery in electrical contact with the ground terminal of the battery, and an electrically conductive portion of the micromotor electrically connected between the battery-supporting socket and said one contact stud, and second means for electrically connecting the other contact stud to a positive terminal of the battery, the second means including an insulated conducting rod extending longitudinally along the micromotor, the front end of the rod being in contact with the other contact stud to urge the same forwardly, and a pair of resilient conductive blades electrically coupled with each other and disposed between the micromotor and the battery, one of the resilient blades bearing against the positive terminal of the battery and the other resilient blade engaging with the rear end of the rod to urge the rod forwardly.

3. The combination according to claim 1 wherein the battery-charging device includes an automatic circuit for switching the device between a quick-charging operation and a slow-charging operation during charging of the battery according to the output voltage of the battery, the automatic circuit including an operational amplifier operative to compare the output voltage of the battery with an adjustable threshold voltage of the operational amplifier to selectively undergo the quick- and slow-charging operations.

4. The combination according to claim 3 wherein the battery-charging device includes a pair of pilot lights, one light being energized when the quick-charging operation is being carried out and the other light being energized when the slow-charging operation is being carried out.

5. A dental handpiece comprising: a front piece having at the front end portion thereof a tool holder for driveably supporting a tool and illuminating means for illuminating an operating range of the tool during use of the dental handpiece; a rear piece having a rechargeable battery therein for supplying electric power to the illuminating means, the rear piece being attachable at the front end thereof to the rear end of the front piece during use of the dental handpiece and being detachable at the front end thereof from the rear end of the front piece during charging of the rechargeable battery; and connecting means for electrically connecting the illuminating means and the rechargeable battery with each other when the front and rear pieces are attached to each other, the connecting means including first connecting means disposed at the rear end of the front piece and electrically connected to the illuminating means, and second connecting means disposed at the front end of the rear piece and electrically connected to the battery, the first and second connecting means being configured relative to each other such that when the front and rear pieces are detachably attached to each other, the first and second connecting means are electrically coupled with each other with a positional allowance for relative circumferential displacement therebetween.

6. A dental handpiece according to claim 5 wherein the front piece comprises a head section for accommodating therein the tool holder and the illuminating means, a front section extending rearwardly from the hea section, and a rear section separably engageable at the front end thereof with the rear end of the front section during use of the dental handpiece.

7. A dental handpiece according to claim 5 wherein the illuminating means comprises a bulb.

8. A dental handpiece according to claim 5 wherein the rear piece includes driving means connectable to the tool holder when the front and rear pieces are attached to each other for driving the tool holder.

9. A dental handpiece according to claim 8 wherein the driving means includes a micromotor.

10. A dental handpiece according to claim 9 wherein the rear piece includes a battery socket disposed rearwardly from the micromotor for receiving therein the battery.

11. A dental handpiece according to claim 10 wherein the rear piece includes conductive means for electrically connecting the second connecting means to the battery.

12. A dental handpiece according to claim 11 wherein the conductive means comprises a pair of separate conductive means electrically connected to the positive and negative terminals of the battery, respectively.

13. A dental handpiece according to claim 12 wherein one of the separate conductive means comprises an electrically conductive battery socket in contact with the negative terminal of the battery, and an electrically conductive portion of the micromotor electrically connected between the second connecting means and the electrically conductive battery socket.

14. A dental handpiece according to claim 12 wherein the other of the separate conductive means comprises a pair of electrically conductive blades electrically coupled with each other and disposed between the battery and the micromotor, one of the blades being biased against the positive terminal of the battery to make electrical contact therebetween, and an electrically conductive rod electrically connected between the second connecting means and the other blade and being biased forwardly by the other blade.

15. A dental handpiece according to claim 5 wherein the first connecting means comprises a pair of concentric annular tracks electrically insulated from each other.

16. A dental handpiece according to claim 15 wherein the second connecting means comprises a pair of contact pins protruding forwardly from the front end of the rear piece and being arranged to radially correspond to respective ones of the annular tracks.

17. A dental handpiece according to claim 16 including means for urging the contact pins forwardly against the annular tracks when the first and second connecting means are coupled with each other.

18. In combination: a dental handpiece comprising a front piece having at the front end portion thereof a tool holder for driveably supporting a tool and illuminating means for illuminating an operating range of the tool during use of the dental handpiece, the front piece having at the rear end thereof first connecting means electrically connected to the illuminating means, and a rear piece having therein a rechargeable battery and second connecting means disposed at the front end of the rear piece and electrically connected to the battery, the rear piece being attachable at the front end thereof to the rear end of the front piece during use of the dental handpiece such that the first and second connecting means are electrically coupled with each other to supply electric power from the battery to the illuminating means and being detachable at the front end thereof from the rear end of the front piece during charging the rechargeably battery; and charging means having third connecting means for providing a charging current, the charging means being configured to removably receive therein the front end of the rear piece during charging of the battery such that the second and third connecting means are electrically coupled with each other to supply the charging current to the battery.

19. The combination according to claim 18 wherein the first and second connecting means are configured relative to each other such that the first and second connecting means are electrically coupled with each other with a positional allowance for relative circumferential displacement therebetween.

20. The combination according to claim 19 wherein the first connecting means comprises a pair of concentric annular tracks electrically insulated from each other.

21. The combination according to claim 20 wherein the second connecting means comprises a pair of contact pins protruding forwardly from the front end of the rear piece and being arranged to radially correspond to respective ones of the annular tracks.

22. The combination according to claim 19 wherein the second and third connecting means are configured relative to each other such that the second and third connecting means are electrically coupled with each other with a positional allowance for relative circumferential displacement therebetween.

23. The combination according to claim 22 wherein the third connecting means is configured the same as the first connecting means.

24. The combination according to claim 23 wherein the third connecting means comprises a pair of concentric rings electrically insulated from each other.

25. The combination according to claim 24 wherein the second connecting means comprises a pair of contact pins protruding forwardly from the front end of the rear piece and being arranged to radially correspond to respective ones of the concentric rings.

26. The combination according to claim 18 wherein the rear piece has a projection extending forwardly from the front end of the rear piece, and the front piece has therein a recess extending rearwardly from the rear end of the front piece for receiving therein the projection.

27. The combination according to claim 26 wherein the charging means has means defining a cavity for receiving therein the projection.

28. The combination according to claim 18 wherein the charging means includes a charging circuit for producing the charging circuit.

29. The combination according to claim 28 wherein the charging circuit includes a control circuit for controlling the amount of the charging current according to the output voltage of the battery during charging of the battery.

30. The combination according to claim 29 wherein the control circuit includes means for increasing the charging current when the output voltage of the battery is less than a certain value and decreasing the charging current when the output voltage of the battery exceeds a certain value.

31. The combination according to claim 30 wherein the control circuit includes means for indicating whether the output voltage of the battery during charging thereof is above the certain value or below the certain value.

* * * * *